United States Patent [19]
Pearson et al.

[11] Patent Number: 5,133,798
[45] Date of Patent: Jul. 28, 1992

[54] CERTAIN HERBICIDAL 1,2,4-TRIAZOLO[4,5-B]PYRIDINES

[75] Inventors: David P. J. Pearson, Maidenhead; John E. D. Barton, North Stoke; David Cartwright, Lower Earley; Susan P. Barnett, Binfield, all of England

[73] Assignee: Imperial Chemical Industries PLC, London, Great Britain

[21] Appl. No.: 652,816

[22] Filed: Feb. 7, 1991

[30] Foreign Application Priority Data

Feb. 16, 1990 [GB] United Kingdom ............... 9003555

[51] Int. Cl.$^5$ .................... A01N 43/90; C07D 471/04
[52] U.S. Cl. ......................................... 71/92; 546/117
[58] Field of Search ............................. 546/117; 71/92

[56] References Cited

FOREIGN PATENT DOCUMENTS 178708 4/1986 European Pat. Off. .
299446 1/1989 European Pat. Off. .
10065 9/1989 Sri Lanka .
2157679 10/1985 United Kingdom .

*Primary Examiner*—Bernard Dentz
*Attorney, Agent, or Firm*—Joel G. Ackerman

[57] ABSTRACT

A compound of formula (I):

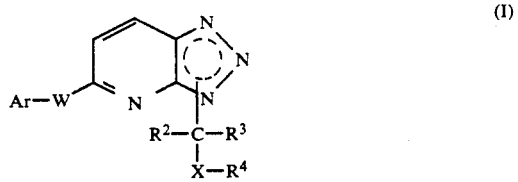

in which
the dotted lines indicate the presence of two double bonds arranged so as to form a fused hetero-aromatic ring system;
Ar is an optionally substituted aryl or heterocyclic ring;
W is O or $NR^1$, where $R^1$ is hydrogen or lower alkyl;
X is $(CH_2)_n$, $CH=CH$, $CH(OR^5)CH_2$, $COCH_2$;
where n is 0, 1 or 2;
$R^2$ and $R^3$ are independently selected from H, optionally substituted alkyl, alkenyl or alkynyl, halogen, $NR^6R^7$ or $R^2$ and $R^3$ together with the carbon to which they are attached form an optionally substituted alkenyl or cycloalkyl group;
$R^4$ is $CO_2R^8$, CN, $COR^8$, $CH_2OR^8$, $CH(OH)R^8$, $CH(OR^8)R^9$, $CSNH_2$, $COSR^8$, $CSOR^8$, $CONHSO_2R^8$, $CONR^{10}R^{11}$, $CONHNR^{10}R^{11}$, $CONHN^+R^{10}R^{11}R^{12}R^{13-}$, $CO_2^-R^{14+}$ or $COON=CR^{10}R^{11}$;
$R^{14+}$ is an agriculturally acceptable cation; and $R^{13-}$ is an agriculturally acceptable anion;
$R^5$, $R^8$ and $R^9$ are independently selected from H or an optionally substituted alkyl, aryl, alkenyl or alkynyl group; and
$R^6$, $R^7$, $R^{10}$, and $R^{12}$ are independently selected from H or an optionally substituted alkyl, alkenyl, aryl or alkynyl group or any two of $R^6$, $R^7$, $R^{10}$, $R^{11}$ and $R^{12}$ together with the atom to which they are attached form a cycloalkyl or heterocyclic ring. Compounds of formula (I) are herbicidal and composition containing them and methods of treatment using them are also described.

11 Claims, No Drawings

CERTAIN HERBICIDAL 1,2,4-TRIAZOLO[4,5-B]PYRIDINES

The present invention relates to novel substituted triazolopyridine derivatives, processes for their preparation, their use as herbicides and herbicidal compositions containing them.

European Patent No. 178,708 A describes certain benzheterocyclyl-phenyl ether derivatives which have herbicidal activity.

According to the present invention there is provided a compound of formula (I):

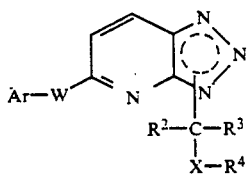

in which
the dotted lines indicate the presence of two double bonds arranged so as to form a fused heteroaromatic ring system;
Ar is an optionally substituted aryl or heterocyclic ring;
W is O or $NR^1$, where $R^1$ is hydrogen or lower alkyl;
X is $(CH_2)_n$, $CH=CH$, $CH(OR^5)CH_2$, $COCH_2$; where n is 0, 1 or 2;
$R^2$ and $R^3$ are independently selected from H, optionally substituted alkyl, alkenyl or alkynyl, halogen, $NR^6R^7$ or $R^2$ and $R^3$ together with the carbon to which they are attached form an optionally substituted alkenyl or cycloalkyl group;
$R^4$ is $CO_2R^8$, CN, $COR^8$, $CH_2OR^8$, $CH(OH)R^8$, $CH(OR^8)R^9$, $CSNH_2$, $COSR^8$, $CSOR^8$, $CONHSO_2R^8$, $CONR^{10}R^{11}$, $CONHNR^{10}R^{11}$, $CONHN+R^{10}R^{11}R^{12}R^{13-}$, $CO_2-R^{14+}$ or $COON=CR^{10}R^{11}$;
$R^{14+}$ is an agriculturally acceptable cation; and $R^{13-}$ is an agriculturally acceptable anion;
$R^5$, $R^8$ and $R^9$ are independently selected from H or an optionally substituted alkyl, aryl, alkenyl or alkynyl group; and
$R^6$, $R^7$, $R^{10}$, $R^{11}$ and $R^{12}$ are independently selected from H or an optionally substituted alkyl, alkenyl, aryl or alkynyl group or any two of $R^6$, $R^7$, $R^{10}$, $R^{11}$ and $R^{12}$ together with the atom to which they are attached form a cycloalkyl or heterocyclic ring.

As used herein the term "alkyl" includes straight or branched chains containing up to 10 carbon atoms preferably from 1 to 6 carbon atoms. The terms "alkenyl" and "alkynyl" refer to unsaturated straight or branched chains having from 2 to 10 and preferably from 2 to 6 carbon atoms. The term "cycloalkyl" includes rings containing from 3 to 9 carbon atoms, preferably from 3 to 6 carbon atoms. The term "alkoxy" includes straight or branched chains containing up to 10 carbon atoms preferably from 1 to 6 carbon atoms.

The term "lower" used in relation to alkyl, alkenyl or alkynyl groups means that the group contains up to 3 carbon atoms.

The term "haloalkyl" and "haloalkoxy" refer to alkyl and alkoxy groups respectively substituted by at least one halogen atom such as fluorine, chlorine or bromine.

A particular haloalkyl group is trifluoromethyl. The term "aryl" includes phenyl and naphthyl The term "heterocyclic" includes rings of up to 10 atoms, preferably up to 6 atoms up to 3 of which are selected from oxygen, nitrogen or sulphur. The term halogen includes fluorine, chlorine, bromine and iodine.

A suitable aryl ring system is phenyl.

Suitable heterocyclic ring systems for Ar are rings of up to 10 atoms, up to 3 of which are selected from oxygen, nitrogen or sulphur, preferably aromatic rings such as pyridine and pyrazole.

Suitable optional substitutents for the aryl or heterocyclic ring systems Ar and aryl groups $R^5$, $R^6$, $R^7$, $R^8$, $R^9$, $R^{10}$, $R^{11}$ and $R^{12}$ are up to 5 preferably up to 3 members selected from halogen (fluoro, chloro, bromo or iodo), lower alkyl, haloalkyl (for example $CF_3$), haloalkoxy (for example $OCF_3$), nitro, cyano, lower alkoxy (for example methoxy) or $S(O)_mR^a$ where m is 0 or 1 and $R^a$ is alkyl (for example thiomethyl, sulphinylmethyl and sulphonylmethyl).

Preferred positions of substitution when the aryl ring Ar is a phenyl ring are the 2, 4 and 6 positions, particularly 2,4,6-tri-substituted rings with a trifluoromethyl group at the 4-position.

Examples of optional substituents for alkyl, alkenyl, alkynyl groups $R^2$, $R^3$, $R^5$, $R^6$, $R^7$, $R^8$, $R^9$, $R^{10}$, $R^{11}$, and $R^{12}$ include one or more groups selected from halo such as fluoro, chloro or bromo; nitro, cyano; aryl such as phenyl; $CO_2R^{15}$, $NHCOR^{15}$ or $NHCH_2CO_2R^{15}$ wherein is hydrogen, $C_{1-6}$ alkyl or an agriculturally acceptable cation; $C_{1-6}$ alkoxy; oxo; $S(O)_mR^1a$ where m and $R^a$ are as hereinbefore defined (for example thiomethyl, sulphinylmethyl and sulphonylmethyl) amino; mono- or di-$C_{1-6}$ alkylamino; $CONR^{16}R^{17}$ wherein $R^{16}$ and $R^{17}$ are independently selected from hydrogen, $C_{1-6}$ alkyl, $C_{2-6}$ alkenyl or $C_{2-6}$ alkynyl or $R^{16}$ and $R^{17}$ are joined together to form a heterocyclic ring having up to 7 ring atoms 3 of which may be selected from oxygen, nitrogen or sulphur An example of a heterocyclic substitutent is tetrahydrofuranyl.

Examples of agriculturally acceptable anions $R^{13-}$ include halide such as iodide.

Examples of agriculturally acceptable cations $R^{14+}$ and $R^{15}$ include sodium, potassium or calcium ions, sulphonium or sulphoxonium ions for example of formula $S(O)_fR^{10}R^{12}$ where f is 0 or 1, or ammonium or tertiary ammonium ions of formula $N+R^{10}R^{11}R^{12}R^{12'}$ where $R^{10}$, $R^{11}$, and $R^{12}$ are as hereinbefore defined and $R^{12'}$ is a group as hereinbefore defined for $R^{12}$. Suitable substituents for alkyl, alkenyl, alkynyl groups in these cations include hydroxy and phenyl. Suitably where any of $R^6$, $R^7$, $R^8$ and $R^9$ in these cations are optionally substituted alkyl, they contain from 1 to 4 carbon atoms.

Particular examples of $R^{10}$, $R^{11}$, $R^{12}$ and $R^{12'}$, in these cations are hydrogen, ethyl, isopropyl, 2-hydroxyethyl and benzyl.

Suitable halo groups $R^2$ and $R^3$ include fluorine, chlorine and bromine.

Suitable heterocyclic rings formed from two of $R^6$, $R^7$, $R^{10}$, $R^{11}$, and $R^{12}$ and the atom to which they are attached are pyrrolidine, piperidine and morpholine.

Suitably $R^1$ is oxygen or a group NH or $NCH_3$. Preferably $R^1$ is oxygen.

Preferably one of $R^2$ or $R^3$ is hydrogen and the other is H or is $C_{1-3}$ alkyl, in particular methyl.

Suitable groups R⁴ include $CO_2R^8$, CN, $CH_2OR^8$, $CONR^{10}R^{11}$, $COON=CR^{10}R^{11}$ or $CONH^+R^{10}R^{11}R^{12}R^{13-}$. Preferably in these groups $R^8$ is selected from hydrogen, alkyl, alkyl substituted by $C_{1-6}$ alkoxy or aryl or alkynyl.

$R^{10}$, $R^{11}$ and $R^{12}$ in these groups are suitably selected from hydrogen or alkyl particularly lower alkyl.

Most preferably $R^4$ is a group $CO_2R^8$ where $R^8$ is $C_{1-6}$ alkyl in particular lower alkyl especially ethyl.

Suitably the group Ar is a group of sub-formula (i)

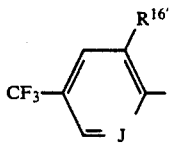

where $R^{16'}$ is hydrogen or halo, and J is N or a group $CR^{17'}$ where $R^{17'}$ is hydrogen or halo Preferably J is $CR^{17'}$ where $R^{17'}$ is halo.

Suitably halo groups $R^{16'}$ and $R^{17'}$ include fluorine, chlorine, bromine and iodine.

Preferably both $R^{16'}$ and $R^{17'}$ are halogen. Suitably one of $R^{16'}$ or $R^{17'}$ is fluorine and the other is chlorine.

Alternatively Ar is an optionally substituted pyrazole group of sub formula (ii)

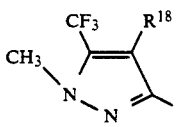

where $R^{18}$ is hydrogen, lower alkyl such as methyl or halogen such as chlorine.

W is preferably oxygen

Preferably X is $(CH_2)_n$ where n is zero or 1, especially zero.

The formula (I) given above is intended to include tautomeric forms of the structure drawn, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intermolecular or intra-molecular hydrogen bonding, or otherwise.

Some of the compounds of the invention can exist in enantiomeric forms. The invention includes both individual enantiomers and mixtures of the two in all proportions.

Particular examples of compounds according to the invention are shown in Tables 1 and 2 below:

TABLE I

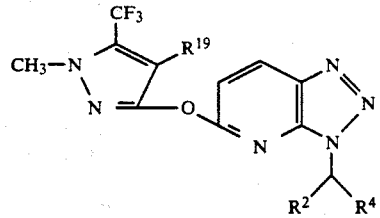

| Compound No | R¹⁹ | R² | R⁴ | Mpt |
|---|---|---|---|---|
| 1 | H | CH₃ | CO₂H | 56–58° C. |

TABLE I-continued

| Compound No | R¹⁹ | R² | R⁴ | Mpt |
|---|---|---|---|---|
| | | | | (dec) |
| 2 | H | CH₃ | CO₂CH₃ | 113–114° C. |
| 3 | H | CH₃ | CO₂CH₂CH₃ | 109–110° C. |
| 4 | H | CH₃ | CO₂(CH₂)₃CH₃ | 65–66° C. |
| 5 | H | CH₃ | CONH₂ | 187–188° C. |
| 6 | H | CH₃ | CONHCH₃ | 201–203° C. |
| 7 | H | CH₃ | CON(CH₃)₂ | 149–152° C. |
| 8 | Cl | H | CO₂H | 169° C. (dec) |
| 9 | Cl | H | CO₂CH₃ | 131–132° C. |
| 10 | Cl | H | CO₂CH₂CH₃ | 120–121° C. |
| 11 | Cl | CH₃ | CH₂OH | 155–156° C. |
| 12 | Cl | CH₃ | CO₂H | 175–177° C. |
| 13 | Cl | CH₃ | CO₂CH₃ | 89–90° C. |
| 14 | Cl | CH₃ | CO₂CH₂CH₃ | 79–80° C. |
| 15 | Cl | CH₃ | CO₂(CH₂)₃CH₃ | gum |
| 16 | Cl | CH₃ | CONH₂ | 163–164° C. |
| 17 | Cl | CH₃ | CN | 93–94° C. |

TABLE II

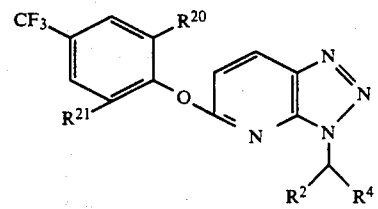

| Compound No | R²⁰ | R²¹ | R² | R⁴ | Mpt |
|---|---|---|---|---|---|
| 18 | H | Cl | H | CO₂H | 164° C. (dec) |
| 19 | H | Cl | H | CO₂CH₃ | 94–95° C. |
| 20 | H | Cl | H | CO₂CH₂CH₃ | 82–83° C. |
| 21 | H | Cl | CH₃ | CH₂OH | 111–112° C. |
| 22 | H | Cl | CH₃ | CO₂H | 156° C. (dec) |
| 23 | H | Cl | CH₃ | CO₂CH₃ | 59–60° C. |
| 24 | H | Cl | CH₃ | CO₂CH₂CH₃ | 64–65° C. |
| 25 | H | Cl | CH₃ | CO₂(CH₂)₂CH₃ | 59–60° C. |
| 26 | H | Cl | CH₃ | CO₂CH(CH₃)₂ | 85–86° C. |
| 27 | H | Cl | CH₃ | CO₂(CH₂)₃CH₃ | gum |
| 28 | H | Cl | CH₃ | CO₂CH₂CH₂OCH₃ | gum |
| 29 | H | Cl | CH₃ | CO₂CH₂C.CH | 70–72° C. |
| 30 | H | Cl | CH₃ | CO₂CH₂(C₆H₅) | 117–118° C. |
| 31 | H | Cl | CH₃ | CO₂NC(CH₃)₂ | gum |
| 32 | H | Cl | CH₃ | CONH₂ | 150–152° C. |
| 33 | H | Cl | CH₃ | CONHCH₃ | 211–212° C. (dec) |
| 34 | H | Cl | CH₃ | CON(CH₃)₂ | 94–96° C. |
| 35 | H | Cl | CH₃ | CONHN(CH₃)₂ | 171–173° C. |
| 36 | H | Cl | CH₃ | CONHN(CH₃)₃I⁻ | 174–175° C. |
| 37 | H | Cl | CH₃ | CN | 103–104° C. |
| 38 | F | Cl | CH₃ | CH₂OH | 106–108° C. |
| 39 | F | Cl | CH₃ | CO₂H | 163° C. (dec) |
| 40 | F | Cl | CH₃ | CO₂CH₃ | 123–124° C. |
| 41 | F | Cl | CH₃ | CO₂CH₂CH₃ | 115–116° C. |
| 42 | F | Cl | CH₃ | CO₂(CH₂)₂CH₃ | 60–62° C. |
| 43 | F | Cl | CH₃ | CO₂(CH₂)₃CH₃ | 48–50° C. |
| 44 | F | Cl | CH₃ | CO₂CH₂CH₂OCH₃ | 55–56° C. |
| 45 | F | Cl | CH₃ | CO₂CH₂C.CH | 87–88° C. |
| 46 | F | Cl | CH₃ | CONH₂ | 162–163° C. |
| 47 | F | Cl | CH₃ | CONHCH₂CH₃ | 172–173° C. |
| 48 | F | Cl | CH₃ | CN | 96–98° C. |
| 49 | F | Cl | CH₃ | CO₂NC(CH₃)₂ | 78–80° C. |

TABLE II-continued

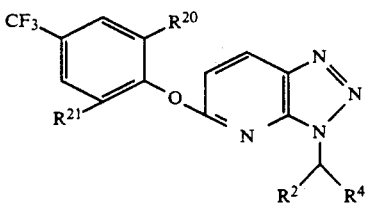

| Compound No | R²⁰ | R²¹ | R² | R⁴ | Mpt |
|---|---|---|---|---|---|
| 50 | F | Cl | H | CH₂OH | 137–138° C. |
| 51 | F | Cl | H | CO₂H | 199° C. (dec) |
| 52 | F | Cl | H | CO₂CH₃ | 115–116° C. |
| 53 | F | Cl | H | CO₂CH₂CH₃ | 99–100° C. |
| 54 | F | Cl | H | CO₂(CH₂)₃CH₃ | 108–109° C. |
| 55 | CH₃O | Cl | CH₃ | CO₂CH₃ | gum |
| 56 | CH₃O | Cl | CH₃ | CO₂H | 184–185° C. |
| 57 | Cl | Cl | CH₃ | CH₂OH | 110–112° C. |
| 58 | Cl | Cl | CH₃ | CO₂H | 193° C. |
| 59 | Cl | Cl | CH₃ | CO₂CH₃ | 123–124° C. |
| 60 | Cl | Cl | CH₃ | CO₂CH₂CH₃ | 114–115° C. |

The structures of all compounds were confirmed by nmr and mass spectrometric techniques.

Compounds of formula (I) may be prepared by reacting a compound of formula (II):

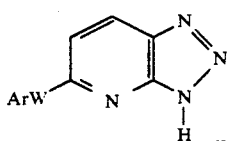

(II)

wherein Ar and W are as defined in relation to formula (I) with a compound of formula (III):

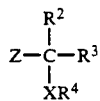

(III)

wherein X, R², R³ and R⁴ are as defined in relation to formula (I) and Z is a leaving group, optionally in the presence of a base. Suitable leaving groups Z include halogen, such as fluorine, bromine and chlorine, and sulphonates such as methanesulphonate and p-toluenesulphonate. Suitable bases for use in the reaction include bases such as sodium hydride, and alkali metal carbonates and hydroxides, or alkoxides.

The reaction is preferably carried out in an organic solvent such as dimethylformamide, dimethylsulphoxide, tetrahydrofuran, acetonitrile, a lower alkanol, or a lower alkyl ketone. Moderate temperatures, for example of from 20° to 90° C. are suitably employed. Conveniently the reaction is carried out at 25° to 30° C.

Compounds of formula (II) can be prepared from compounds of formula (IV):

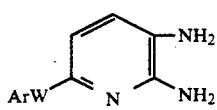

(IV)

wherein Ar and W are as defined in relation to formula (I) by diazotisation for example with nitrous acid e.g. according to the procedure described in Rüfenacht, Helv. Chim. Acta 58,1521, (1975).

Compounds of formula (IV) are prepared by reduction of the corresponding nitro compound of formula (V).

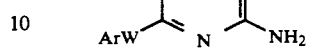

(V)

A wide variety of reducing agents may be used and may be selected from the chemical literature by the skilled worker in the art. The reduction may be carried out for example by using sodium dithionite or tin and hydrochloric acid, iron and hydrochloric acid, or either hydrogen or a suitable hydrogen donor such as sodium borohydride with a palladium on charcoal catalyst. The reaction may be effected in an organic solvent such as a lower alkyl alcohol optionally mixed with water at temperatures of 20° C. to 90° C.

Compounds of formula (V) can be prepared from compounds of formula (VI):

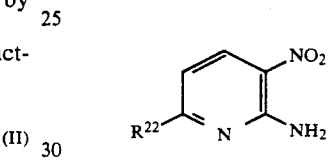

(VI)

in which R²² is halogen such as fluorine, chlorine, bromine or iodine by reaction with compounds of formula (VII):

Ar—WH (VII)

wherein Ar and W are as defined in relation to formula (I) according to the procedure described in Heilmann, Wiss.Z Pedagog Hansch, "Karl Liebknecht" Potsdam, 28,115 (1984) and von Bebenburg, Chem Ztg 103,387 (1979).

Compounds of formula (VI) may be prepared from compounds of formula (VIII):

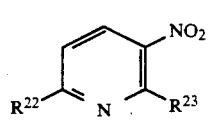

(VIII)

where R²² is as defined above and R²³ is also a halogen atom selected from fluorine, chlorine, bromine or iodine. e.g. according to methods described by Kroon, Rec Trav. Chim, 95,127, (1976).

Compounds of formula (III), (VII) and (VIII) are known compounds or they can be prepared from known compounds by known methods.

This process will produce a mixture of 3 isomers in which the group CR²R³XR⁴ is attached to the triazolopyridine ring at the 1, 2 or 3 positions. In suitable cases the isomers may be separated by conventional procedures e.g. flash chromatography.

An alternative method of preparing compounds of formula (I) which will yield only one isomer where the group CR²R³XR⁴ is attached at the 1 position of the triazolopyridine ring consists of the diazotisation of compounds of formula (IX) using the conditions as for the diazotisation of compounds of formula (IV):

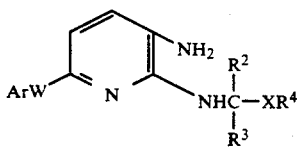

(IX)

where Ar, W, X, $R^2$, $R^3$ and $R^4$ are as defined in relation to formula (I). Compounds of formula (IX) are novel and as such form a further aspect of the invention.

Compounds of formula (IX) can be prepared by reduction of a compound of formula (X):

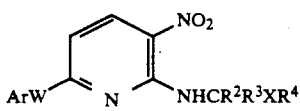

(X)

using methods similar to those described above in relation to the reduction of compound (IV). Compounds of formula (X) are known compounds or they can be prepared from known compounds by conventional methods.

Compounds of formula (X) where Ar is pyrazole are novel and as such form a further aspect of the invention. They can be prepared by the following scheme:

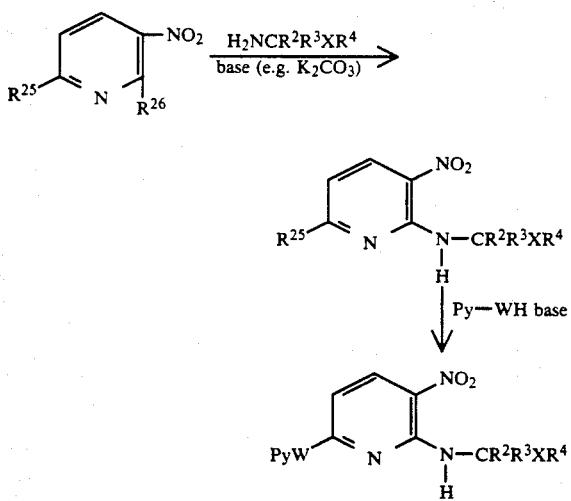

where $R^{25}$ and $R^{26}$ are independently leaving groups such as fluorine, Py is an optionally substituted pyrazole group and W, $R^2$, $R^3$, X and $R^4$ are also defined in relation to formula (I).

Examples of such processes are illustrated in the examples hereinafter.

If desired one or more of the following steps may be carried out :
i) when $R^4$ is alkoxycarbonyl hydrolysing to the corresponding acid.
ii) when $R^4$ is COOH esterifying or forming a salt, amide, sulphonamide, hydrazide or hydrazinium derivative.
iii) when $R^4$ is an alcohol, oxidation to the corresponding acid or aldeghyde.
iv) when $R^4$ is alkoxycarbonyl, reduction to an alcohol.
v) when $R^4$ is an amide, dehydration to the corresponding nitrile.

Steps (i) - (v) above all represent standard chemical transformations and reactants and reaction conditions will be apparent to a chemist. Examples of such transformations are to be found hereinafter.

The compounds of formula (I) are active as herbicides and therefore, in a further aspect the invention provides a process for severely damaging or killing unwanted plants which process comprises applying to the plants, or to the growth medium of the plants, an effective amount of a compound of formula (I) as hereinbefore defined.

The compounds of formula (I) are active against a broad range of weed species including monocotyledenous and dicotyledonous species They may show some selectivity towards certain species; they may be used as selective herbicides in rice and wheat crops.

The compounds of formula (I) may be applied directly to the plant (post-emergence application) or to the soil before the emergence of the plant (pre-emergence application). They are particularly useful when applied post-emergence The compounds of formula (I) may be used on their own to inhibit the growth of, severely damage, or kill plants but are preferably used in the form of a composition comprising a compound of the invention in admixture with a carrier comprising a solid or liquid diluent.

Therefore, in yet a further aspect, the invention provides plant growth inhibiting, plant damaging, or plant killing compositions comprising a compound of formula (I) as hereinbefore defined and an inert carrier or diluent.

Compositions containing compounds of formula (I) include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01% to 2% of active ingredient, while concentrated compositions may contain from 20% to 90% of active ingredient, although from 20% to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type or mixtures thereof. The cationic agents are, for example, quaternary ammonium compounds (e.g. cetyltrimethylammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol (e.g. Agral 90) or octylcresol. Other non-ionic agents are the partial esters derived from long chain fatty acids and hexitol anhydrides, for example sorbitan monolaurate; the condensation products of the partial ester with ethylene oxide; and the lecithins; silicone surface active agents (water soluble surface active agents having a skeleton which comprises a siloxane chain e.g. Silwet L77). A suitable mixture in mineral oil is Atplus 411F.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogenous for a sufficient time to enable them to be applied by conventional spray equipment. Concentrates conveniently contain 20-90%, preferably 20-70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and suacorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.01 to 20 kilograms per hectare is suitable while from 0.025 to 10 kilograms per hectare may be preferred.

The compositions of the invention may comprise, in addition to one or more compounds of the invention, one or more compounds not of the invention but which possess biological activity. Accordingly in yet a still further embodiment the invention provides a herbicidal composition comprising a mixture of at least one herbicidal compound of formula (I) as hereinbefore defined with at least one other herbicide.

The other herbicide may be any herbicide not having the formula (I). It will generally be a herbicide having complementary action in the particular application.

Examples of useful complementary herbicides include:

A. benzo-2,1,3-thiadiazin-4-one-2,2-dioxides such as bentazone;
B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, clopyralid, and their derivatives (eg. salts, esters and amides);
C. 1,3 dimethylpyrazole derivatives such as pyrazoxyfen, pyrazolate and benzofenap;
D. Dinitrophenols and their derivatives (eg. acetates) such as dinoterb, dinoseb and its ester, dinoseb acetate;
E. dinitroaniline herbicides such as dinitramine, trifluralin, ethalfluralin, pendimethalin, oryzalin;
F. arylurea herbicides such as diuron, flumeturon, metoxuron, neburon, isoproturon, chlorotoluron, chloroxuron, linuron, monolinuron, chlorobromuron, daimuron, methabenzthiazuron;
G. phenylcarbamoyloxyphenylcarbamates such as phenmedipham and desmedipham;
H. 2-phenylpyridazin-3-ones such as chloridazon and norflurazon;
I. uracil herbicides such as lenacil, bromacil and terbacil;
J. triazine herbicides such as atrazine, simazine, aziprotryne, cyanazine, prometryn, dimethametryn, simetryne, and terbutryn;
K. phosphorothioate herbicides such as piperophos, bensulide, and butamifos;
L. thiolcarbamate herbicides such as cycloate, vernolate, molinate, thiobencarb, butylate*, EPTC*, triallate, di-allate, esprocarb, tiocarbazil, pyridate, and dimepiperate;
M. 1,2,4-triazin-5-one herbicides such as metamitron and metribuzin;
N. benzoic acid herbicides such as 2,3,6-TBA, dicamba and chloramben;
O. anilide herbicides such as pretilachlor, butachlor, alachlor, propachlor, propanil, metazachlor, metolachlor, acetochlor, and dimethachlor;
P. dihalobenzonitrile herbicides such as dichlobenil, bromoxynil and ioxynil;
Q. haloalkanoic herbicides such as dalapon, TCA and salts thereof;
R. diphenylether herbicides such as lactofen, fluroglycofen or salts or ester thereof, nitrofen, bifenox, aciflurofen and salts and esters thereof, oxyfluorfen, fomesafen, chlornitrofen and chlomethoxyfen;
S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;
T. cyclohexanedione herbicides such as alloxydim and salts thereof, sethoxydim, cycloxyidim, tralkoxydim, and clethodim;
U. sulfonyl urea herbicides such as chlorosulfuron, sulfometuron, metsulfuron and esters thereof; benzsulfuron and esters thereof such as DPX-M6313, chlorimuron and esters such as the ethyl ester thereof pirimisulfuron and esters such as the methyl ester thereof, 2-[3-(4-methoxy-6-methyl-1,3,5-triazin-zyl)-3-methylureidosulphonyl) benzoic acid esters such as the methyl ester thereof (DPX-LS300) and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate and glufosinate and their salts and esters, sulphosate and bialaphos;

Y. organoarsenical herbicides such as monosodium methanearsonate (MSMA);

Z. herbicidal amide derivative such as napropamide, propyzamide, carbetamide, tebutam, bromobutide, isoxaben, naproanilide and naptalam;

AA. miscellaneous herbicides including ethofumesate, cinmethylin, difenzoquat and salts thereof such as the methyl sulphate salt, clomazone, oxadiazon, bromofenoxim, barban, tridiphane, flurochloridone, quinchlorac dithiopyr and mefanacet;

BB. Examples of useful contact herbicides include:
bipyridylium herbicides such as those in which the active entity is paraquat and those in which the active entity is diquat;

These compounds are preferably employed in combination with a safener such as dichlormid.

The following Examples illustrate the invention:

EXAMPLE 1

This example illustrates the preparation of compound 1

Step A

DL-Alanine ethyl ester hydrochloride (30.0g, 0.195 mol) and potassium carbonate (56.5g, 0.39mol) were stirred at room temperature in acetonitrile (350ml) for 30 minutes. 2,6-Difluoro-3-nitropyridine (31.2g, 0.195mol) was added dropwise, over 20 minutes, and when the addition was complete the reaction mixture was stirred at room temperature for 3 hours. The reaction mixture was poured into water and extracted with ethyl acetate. The organic extracts were combined, dried (MgSO$_4$) and the solvent removed under reduced pressure to afford a yellow liquid which solidified on standing. The solid was triturated with hexane and the solvent removed from the soluble fractions leaving ethyl DL-2-[6-fluoro-3-nitropyridyl-2-amino]propionate (26.7g) as a yellow solid m.p. 49–51°. Further product (8.0g) was obtained by subjecting the hexane insoluble residue to purification by flash column chromatography on silica gel, eluting with hexane/ethyl acetate (2:1).

Step B

The fluoropyridine obtained in step A (25.7g, 0.10mol), 3 hydroxy-1-methyl-5-trifluromethyl-1H-pyrazole (16.6g, 0.10mol) and potassium carbonate (13.8g, 0.10mol) were heated together in dimethylsulphoxide (200ml) at 80° C. for 2 hours. After cooling, the reaction mixture was poured into water and extracted with ethyl acetate. The organic extracts were combined, dried (MgSO$_4$) and the solvent removed under reduced pressure to afford a yellow-brown residue. Trituration with hexane gave an orange-yellow solid (29.4g) which was further purified by flash column chromatography on silca gel eluting with hexane/ethyl acetate (2:1) to give ethyl DL 2-[6-(1-methyl-5-trifluoromethyl-1H-pyrazol-3-yloxy)-3-nitropyridyl-2-amino]propionate as an orange-yellow solid m.p. 83–84°.

Step C

The nitropyridine obtained in step B (29.4g, 73.4 mmol) was dissolved in tetrahydrofuran (150ml) and isopropanol (200ml) and a solution of sodium hydroxide (3.23g, 80.7 mmol) in water (32ml) added. The mixture was stirred at room temperature for 3 hours and then the solvent evaporated under reduced pressure to yield an orange-red solid. The residue was taken up in water, acidified to pH2 with concentrated aqueous hydrochloric acid and extracted with dichloromethane. The organic extracts were combined, dried (MgSO$_4$) and the solvent removed under reduced pressure to afford an orange-yellow solid. The solid was triturated with 60–80 petroleum ether to give an orange-yellow solid (21.9g) which was further purified by flash column chromatography on silica gel, eluting with chloroform/ethanol (9:1) to give DL 2-[6-(1-methyl-5-trifluoromethyl-1H-pyrazol 3-yloxy)-3-nitropyridyl-2-amino]propionic acid m.p 148–150°.

Step D

A solution of sodium borohydride (1.38g, 36.3 mmol) in water (30ml) was added to a suspension of 10% palladium on charcoal (0.25g) in water (10ml) under an atmosphere of nitrogen. A solution of the acid obtained in Step C (7.42g, 18.2mmol) in 2M aqueous sodium hydroxide solution (60ml) was added dropwise, maintaining the internal temperature below 30° C. When the addition was complete the mixture was stirred at room temperature for 3 hours, the catalyst removed by filtration through celite, and the filtrate acidified by addition of concentrated aqueous hydrochloric acid. The solution was cooled to 0° C. in an ice/salt bath and a solution of sodium nitrite (2.51g, 36.4mmol) in water (20ml) added dropwise at such a rate that the internal temperature did not rise above 5° C. When the addition was complete the reaction mixture was allowed to warm to room temperature and stirred for a further 1 hour, and then extracted with ethyl acetate. The organic extracts were combined, dried (MgSO$_4$) and the solvent removed under reduced pressure to afford a dark brown solid. Trituration with 60–80 petroleum ether gave a dark brown solid (5.58g) which was further purified by flash column chromatography on silica gel eluting with chloroform/ethanol (9:1) to give compound 1, DL 2-[6-(1-methyl-5-trifluoromethyl-1H-pyrazol-3-yloxy) 1,2,3-triazolo-[4,5-b]pyridinyl-1-]propionic acid as a brownish-yellow solid m.p. 56–58° C.(dec). Compounds 8 and 12 were prepared by analogous processes using appropriate reactants.

EXAMPLE 2

This Example illustrates the preparation of compound 2.

DL 2-[6-(1-methyl-5-trifluoromethyl-1H-pyrazol-3-yloxy)-1,2,3-triazolo-[4,5-b]pyridinyl-1-]propionic acid (0.60g, 1.69 mmol) was heated under reflux in thionyl chloride (10ml) for 2 hours. The mixture was cooled to room temperature and the solvent removed under reduced pressure. The residue was taken up in methanol (5ml) and 4-dimethylaminopyridine (0.23g, 1.88mmol) added. The mixture was stirred at room temperature for 2 hours then heated under reflux for a further 1 hour, cooled and partitioned between water and chloroform. The organic extracts were combined, dried (MgSO$_4$) and the solvent removed under reduced pressure. The residue was purified by flash column chromatography on silica gel, eluting with ethyl acetate/60–80 petroleum ether (1:2) to afford compound 2, methyl DL 2-[6-(1-methyl-[4,5-b]-trifluoromethyl-lH-pyrazol-3-yloxy) -1,2,3-triazolo-[4-5-b]pyridinyl-1]-propionate (0.34g) as a pale yellow solid m.p 113–114° C.

EXAMPLE 3

This Example illustrates the preparation of Compound 4. n-Butanol (1ml) was added to a solution of DL 2-[6-(1-methyl-5-trifluoromethyl-lH-pyrazol-3-yloxy)-1,2,3 -triazolo-[4,5-b]-pyridinyl-3-]propionic acid (0.80g, 2.25mmol) and 4-dimethylaminopyridine (0.30g, 2.47mmol) in 1,2-dichloroethane (10ml) and the mixture cooled to 0° in an ice-salt bath. 1,3-Dicyclohexylcarbodiimide (0.76g, 3.70mmol) was added portionwise and the reaction mixture allowed to warm to room temperature, and then stirred for a further 4 hours. The precipitated urea was removed by filtration, the filtrate evaporated and the residue purified by preparative thin layer chromatography, eluting with hexane/ethyl acetate (2:1). Trituration with 60–80 petroleum ether gave compound 4, n-butyl DL 2-[6-(1-methyl-5-trifluoromethyl-lH-pyrazol-3-yloxy)-1,2,3 -triazolo-[4,5-b]-pyridinyl-1-]propionate (0.19g) as a pale orange solid m.p. 65–66°.

Compounds 3, 9, 10, 13, 14 and 15 were prepared by analogous procedures using appropriate reactants.

EXAMPLE 4

This Example illustrates the preparations of Compound 7.

N,N'-carbonyl diimidazole (0.59g, 3.61mmol) was added to a solution of DL 2-[6-(1-methyl-5-trifluoromethyl-lH-pyrazol-3-yloxy)-1,2,3-triazolo-[4,5-b]-pyridinyl-1-]-propionic acid (0.93g, 2.61 mmol) in tetrahydrofuran (20ml) and the mixture was stirred at room temperature for 2 hours. Gaseous dimethylamine was bubbled through the solution cautiously until the exothermic reaction had ceased, and then the mixture was stirred at room temperature for a further 1 hour. The solvent was removed under reduced pressure and the residue taken up in ethyl acetate, washed successively with saturated aqueous sodium carbonate solution and water, dried (MgSO$_4$) and the solvent evaporated under reduced pressure to give a dark brown residue. Purification by flash column chromatography on silica gel, eluting with ethyl acetate gave compound 7, N,N-dimethyl DL 2-[6-(1-methyl-5-trifluoromethyl-lH-pyrazol-3-yloxy) -1,2,3-triazlo-[4,5-b]-pyridinyl-1-]propionamide (0.13g) as an off-white solid m.p. 149-152° C.

Compound 5 was prepared by an analogous process using appropriate reactants.

EXAMPLE 5

This Example illustrates the preparation of Compound 11.

Step A

Potassium carbonate (30.4g, 0.22mol) was added to a solution of DL 2-aminopropanol (16.5g 0.22mol) in acetonitrile (150ml) and the reaction mixture was stirred at room temperature for thirty minutes. The mixture was cooled in an ice bath and 2,6-difluoro-3-nitropyridine (17.6g, 0.20mol) was added dropwise at such a rate that the temperature of the reaction mixture was maintained below 30° C. When the addition was complete the reaction mixture was stirred at room temperature for 24 hours. The mixture was diluted with diethyl ether (200ml) and washed with water (200ml). The aqueous phase was extracted with diethyl ether (2×100ml). The organic extracts were combined, dried, (MgSO$_4$) filtered and evaporated under reduced pressure and the residue further purified by flash column chromatography on silica gel, eluting with ethyl acetate/60–80 petroleum ether (3:1) to give DL 2-[6-fluoro-3-nitropyridyl-2-amino]propan-1-ol (20.4g) as a colourless oil.

Step B

The fluoropyridine obtained in Step A (3.23g, 15mmol), 4-chloro-3-hydroxy-1-methyl-5-trifluoromethyl-lH-pyrazole (3.01g, 15mmol) and potassium carbonate (2.07g, 15mmol) were stirred together in refluxing acetonitrile (40ml) for 2 hours and then cooled to room temperature. The reaction mixture was poured into water and extracted with ethyl acetate. The organic extracts were combined, dried (MgSO$_4$) and the solvent evaporated under reduced pressure. The residue was triturated with 60-80 petroleum ether to give DL 2-[6-(4-chloro-1-methyl-5-trifluoromethyl-lH-pyrazol-3-yloxy) -3-nitropyridyl-2-amino]propan-1-ol (4.87g) as a pale brown solid m.p 109–111°.

Step C

10% palladium on charcoal (0.15g) was suspended in water (10ml) and a solution of sodium borohydride (1.17g, 31mmol) in water (20ml) was added dropwise. When the addition was complete a solution of the nitropyridine prepared above (4.87g, 12mmol) in methanol (30ml) and tetrahydrofuran (15ml) was added dropwise. The reaction mixture was stirred at room temperature for one hour, then filtered through celite, the filtrate acidified with dilute aqueous hydrochloric acid and the solvent removed under reduced pressure. The residue was taken up in water and extracted with ethyl acetate. The combined organic extracts were dried (MgSO$_4$), the solvent evaporated under reduced pressure and the residue further purified by flash column chromatography on silica gel eluting with ethyl acetate/hexane (1:1) to give DL 2-[3-amino-6-(4-chloro-1-methyl-5-trifluoromethyl-lH-pyrazol-3-yloxy)-pyridyl-2-amino]-propan-1-ol (0.85g).

Step D

The amine obtained in Step C (0.85g, 2.3mmol) was suspended in water (7ml) and acidified with concentrated hydrochloric acid. The mixture was cooled in an ice/salt bath and a solution of sodium nitrite (0.40g, 5.8mmol) in water (5ml) was added dropwise. The reaction mixture was kept below 5° for 30 minutes and then allowed to warm to room temperature. The mixture was extracted with ethyl acetate; the organic extracts were dried (MgSO$_4$) and the solvent evaporated under reduced pressure. The residue was further purified by flash column chromatography on silica gel, eluting with ethyl acetate/hexane (1:1) to give compound 11, 2-[6-(4-chloro - 1 - methyl - 5 - trifluoromethyl - 1H-pyrazol -3 - yloxy) - 1,2,3 - triazolo[4,5 - b] - pyridinyl - 1]propan - 1 - ol (0.29g) as an off-white solid m.p 155–156° C.

EXAMPLE 6

This Example illustrates the preparation of compound 14.

Step A 2,6-difluoro-3-nitropyridine (14.68g,91.8mmol) was added to a mixture of DL-alanine ethyl ester hydrochloride (14.09g 92mmol) and potassium carbonate (25.3g, 183mmol) in acetonitrile (200ml) and the mixture stirred for 2 hours at room temperature. The reaction mixture was poured into water and extracted several times with ethyl acetate; the combined extracts were dried (MgSO$_4$) and the solvent removed in vacuo leaving a viscous orange-yellow residue which solidified on standing. The solid was triturated with hexane and the solvent removed from the hexane soluble fraction leaving ethyl DL-2-[6-fluoro-3-nitropyridyl-2-amino]propionate as a yellow solid m.p. 49–51° C.

Step B

The fluoropyridine obtained in step A (2.57g 10mmol), 4-chloro-3-hydroxy-1-methyl-5-trifluoromethyl-1H-pyrazole (2g, 10mmol) and potassium carbonate (1.38g, 10mmol) were heated in dimethylsulphoxide (20ml) at 80° C. for 2 hours. After cooling, the reaction mixture was poured into water and extracted several times with ethyl acetate. The combined extracts were dried (MgSO$_4$) and the solvent removed in vacuo leaving a yellow-brown residue This was purified by column chromatography on silica gel eluting with hexane/ethyl acetate (2:1) giving ethyl DL 2-[6-(4-chloro-1-methyl-5-trifluoromethyl-1H-pyrazol-3-yloxy)-3-nitropyridyl-2-amino]propionate as a yellow viscous gum which solidified on standing m p. 68–70° C.

Step C

The propionate obtained in step B (2.5g, 5.7mmol) in tetrahydrofuran (10ml) was diluted with isopropanol (25ml) followed by addition of a solution of sodium hydroxide (0.25g,6.28mmol) in water (2.5ml). The reaction mixture was stirred at room temperature for 4 hours. The solvent was then removed in vacuo leaving a viscous orange-red residue (2.6g). This residue was added in 2M aqueous sodium hydroxide (40ml) over 10 minutes to a stirred suspension of 10% palladium on charcoal (100mgs) and sodium borohydride (460mg) in water (15ml); the solutions being kept under nitrogen The reaction mixture was stirred at room temperature for 3 hours and then filtered thorough celite to afford a light brown aqueous solution. The filtrate was carefully acidified by addition of concentrated hydrochloric acid and then cooled to 0° C. in an ice/salt bath. A solution of sodium nitrite(835mg, 12.1mmol) in water (8ml) was added dropwise with stirring maintaining the temperature of the solution at less than 0° C. When the addition was complete the stirred solution was allowed to warm to room temperature and then extracted several times with ethyl acetate The combined extracts were dried (MgSO$_{04}$) and the solvent removed under reduced pressure leaving a viscous brown residue (1.6g).

The residue was dissolved in dichloroethane (40ml) and ethanol (0.4ml), dimethylaminopyridine (256mg) and dicyclohexylcarbodiimide (848mg) added sequentially The mixture was heated under reflux for 8 hours and, after cooling, poured into water and extracted several times with chloroform. The combined extracts were dried (MgSO$_4$) and the solvent removed under reduced pressure leaving an orange-yellow viscous residue which was further purified by column chromatography on silica gel using hexane/ethyl acetate (1:1). Trituration with petrol gave compound 14, ethyl DL 2-[6-(4-chloro-1-methyl-5-trifluoromethyl-pyrazolyl-3-yloxy) -1,2,3,triazolo [4,5-b]pyridinyl-1-]propionate as a pale yellow solid m.p. 79–80° C.

EXAMPLE 7

This Example illustrates the preparation of Compound No. 16.

DL 2-[6-(4-chloro-1-methyl-5-trifluoromethyl-1H-pyrazol-3-yloxy)-1,2,3-triazolo[4,5-b]pyridinyl-1-]-propionic acid (0.80g, 2.05mmol) was heated under reflux with thionyl chloride (10ml) for 1 hour. The mixture was cooled to room temperature and the solvent removed under reduced pressure The residue was cooled in an ice-salt bath and excess aqueous ammonia solution (sp.gr. 0.88) added. The reaction mixture was stirred at room temperature for 30 minutes and then extracted with chloroform. The organic extracts were combined, washed with water, dried (MgSO$_4$) and evaporated under reduced pressure. The residue was purified by flash column chromatography on silica gel eluting with ethyl acetate to give compound No. 16, DL 2-[6-(4-chloro-1-methyl-5-trifluoromethyl-1H-pyrazol-3-yloxy) -1,2,3-triazolo-[4,5-]pyridinyl-1-]propionamide (0.58g) as a solid m.p 163–164° C.

Compound No. 6 was prepared by an analogous process using appropriate reactants.

EXAMPLE 8

This Example illustrates the preparation of Compound No. 17.

Trichloroacetyl chloride (0.28g, 1.54 mmol) in dichloromethane (2ml) was added to a mixture of DL 2-[6-(4-chloro-1-methyl-5-trifluoromethyl-1H-pyrazol-3-yloxy)-1,2,3-triazolo-[4,5-b]-pyridinyl-1-]propionamide (0.55g, 1.47mmol) and triethylamine (0.30g, 2.96mmol) in dichloromethane (20ml) at such a rate that the temperature of the reaction was maintained below 5° C. The reaction mixture was allowed to warm to room temperature and stirred for 1 hour. The solvent was removed under reduced pressure and diethyl ether added to residue. The etheral solution was filtered, the filtrate evaporated in vacuo, and the residue purified by flash column chromatography on silica gel eluting with ethyl acetate/hexane (1:1) to give Compound No. 17, DL 2-[6-(4-chloro-1-methyl-5-trifluoromethyl-1H-pyrazol-3-yloxy) -1,2,3-triazolo-[4,5-b] -pyridinyl-1-]propionitrile (0.35g) as a colourless solid m.p. 93–94° C.

Compound No. 48 was prepared by an analogous process appropriate reactants.

EXAMPLE 9

This Example illustrates the preparation of Compounds Nos. 21, 22 and 23.

Step A

DL-2-aminopropanol (17.5ml, 0.22mol) and potassium carbonate (30.4g, 0.22mol) were stirred together in acetonitrile (150ml) at room temperature for 30 minutes and then cooled in an ice-bath A solution of 2,6-difluoro-3-nitropyridine (26.4g, 0.20mol) in acetonitrile (80ml) was added dropwise at such a rate that the internal temperature never rose above 30° C. Once the addition was complete the reaction mixture was stirred for 24 hours. The reaction mixture was diluted with diethyl ether (200ml) and washed with water (200ml). The aqueous phase was extracted with diethyl ether (2×100ml) and the organic extrcts combined, dried (MgSO4) and evaporated under reduced pressure. The residue was further purified by flash column chromatography on silica gel, eluting with ethyl acetate/60-80 petroleum ether (1:3) to give DL-2-[6-fluoro-3-nitropyridyl-2-amino) propan-1-ol (20.4g) as a yellow oil.

Step B

The fluoropyridine obtained in Step A (6.46g, 0.03mol), 2-chloro-3-hydroxybenzotrifluoride (5.90g, 0.03mol) and potassium carbonate (4.14g, 0.03mol) were heated together in refluxing acetonitrile (80ml) for 2 hours. The mixture was cooled to room temperature and then poured into water and extracted with ethyl acetate. The organic extracts were combined, washed with water, dried (MgSO4) and the solvent removed under reduced pressure to give DL-2-[6-(2-chloro-4-trifluoromethylphenoxy) -3-nitropyridyl-2-]-aminopropan-1-ol (11.76g) as a yellow oil, used without further purification in the next step.

Step C

10% Palladium on charcoal (0.50g) was suspended in water (35ml) and a solution of sodium borohydride (3.99g, 0.105mol) in water (60ml) was added dropwise, and once the addition was complete the reaction mixture was stirred at room temperature for 1 hour.

The catalyst was removed by filtration, the filtrate acidified to pH5 with 2N aqueous hydrochloric acid and the solvent evaporated under reduced pressure The residue was taken up in water, the mixture neutralised with saturated aqueous sodium bicarbonate solution and then extracted with ethyl acetate. The combined extracts were dried (MgSO4) and the solvent removed under reduced pressure to afford a dark purple residue. Trituration with hexane afforded a pale blue solid (10.02g) used directly in the next step.

Step D

The amine obtained in Step C. (10.0g, 0.03mol) was suspended in water (90ml), acidfied with concentrated hydrochloric acid and cooled in an ice/salt bath.

A solution of sodium nitrite (4.75g, 0.07mol) in water (50ml) was added dropwise at such a rate that the internal temperature was maintained below 5° C. and once the addition was complete the reaction was stirred for 30 minutes, and then allowed to warm to room temperature. The mixture was extracted with ethyl acetate and the organic extracts combined, dried (MgSO4) and the solvent removed under reduced pressure to give a dark brown residue which was further purified by flash column chromatography on silica gel eluting with hexane/ethyl acetate (1:1) to give Compound No. 21, DL-2-[6-(2-chloro-4-trifluoromethylphenoxy)-1,2,3-triazolo [4,5-b]pyridinyl-1]-propan-1-ol (5.84g) as an off-white solid m.p 111–112° C. Compounds No. 38, 50 and 57 were prepared by an analogous process using appropriate reactants.

Step E

Jones reagent was prepared according to Organic Synthesis (1965), 45, 28. Thus, chromium trioxide (6.7g) was dissolved in water (13ml). To this was added concentrated sulphuric acid (5.8ml) and the precipitated salts redissolved with water (5ml).

A solution of compound No. 21, prepared in Step D (2.50g, 6.7mmol) was dissolved in acetone (60ml) and the mixture cooled in an ice-bath. Jones reagent, prepared above, was added in aliquots (0.5ml) until 8.5ml had been added. The mixture was allowed to warm slowly to room temperature and stirring continued for 17 hours. Isopropanol was added to consume excess Jones reagent and the precipitated salts removed by filtration.

The filtrate was concentrated, the mixture taken up in ethyl acetate and washed with water, dried (MgSO4) and evaporated under reduced pressure. The residue was triturated with hexane to afford Compound No. 22, DL-2-[6-(2-chloro-4-trifluoromethylphenoxy)-1,2,3-triazolo [4,5-b]pyridinyl-1]propionic acid (2.34g) as a colourless solid m.p 156° C. (dec). Compounds No. 18, 39, 51 and 58 were prepared by analogous processes using appropriate reactants.

Step F

Compound No. 22 prepared above (0.81 g, 2.1 mmol) was suspended in dichloromethane (10 ml ). Methanol (1 ml) and 4-dimethylaminopyridine (0.27 g, 2.2 mmol) were added, followed by dicyclohexylcarbodiimide (0.45 g, 2.2 mmol) and the reaction mixture was stirred at room temperature for 5 hours and then heated under reflux for 1 hour. The mixture was cooled to room temperature, filtered and the filtrate evaporated. The residue was purified by flash column chromatography on silica gel, eluting with hexane/ethyl acetate (2:1) to give Compound No. 23, methyl DL-2-[6-(2-chloro-4-trifluoromethylphenoxy)-1,2,3-triazolo [4,5-b]pyridinyl-1]proprionate (0.21 g) as a colourless solid m.p. 59–60° C.

Compounds No. 19, 20, 24, 25, 26, 27, 28, 29, 40, 41, 42, 43, 44, 45, 49, 52, 53, 54, 59 and 60 were prepared by an analogous process using appropriate reactants, except that is some cases 1,2-dichloroethane was employed as a solvent and it was found that heating of the reaction mixture was not always an essential requirement.

EXAMPLE 10

This example describes the preparation of compound 24.

Step A 2-chloro-3-hydroxybenzotrifluoride (0.983 g 5 mmol) was stirred in an acetonitrile (10 cm$^3$) solution containing potassium carbonate (0.69 g 5 mmol) for 1 hour. Ethyl 2-[6-fluoro-3nitropyridinyl-2-amino]propionate (1.285 g 5mmol) in acetaonitrile (10 cm$^3$) was added dropwise at room temperature. When the addition was complete the reaction mixture was heated under reflux for 2 hours, allowed to cool and poured into water. The aqueous mixture was extracted using ethyl acetate, the combined extracts washed with water and dried (MgSO4). The solvent was removed under reduced pressure leaving an orange-yellow gum which crystallised on standing. Trituration of the solid with 60–80 petroleum ether gave ethyl DL 6-[6-(2-chloro-4-trifluoromethylphenoxy)-3-nitro-pyridinyl-2-amino]propionate as yellow solid m.p. 72-3° c.

Step B

The ester obtained in step A (3.97 g 9.4 mmol) in tetrahydrofuran (20 cm$^3$) and isopropanol (40 cm$^3$) was stirred at room temperature and a solution of sodium hydroxide (0.414 g 10.4 mmol) in water (4 cm³) was added. After stirring for 5 hours the solvent was removed at reduced pressure leaving the required sodium salt as an orange-brown solid (3.78 g) which was used without further purification.

Step C

A solution of sodium borohydride (0.692 g 18.2 mmol) in water (15 cm³) was added dropwise to a stirred suspension of 10% pallodium on charcoal (150 mg) in water (8 cm³) kept under nitrogen. To this mixture was added dropwise a suspension of the diarylether sodium salt produced in step B (3.78 g 9.1 mmol) in 2M aqueous sodium hydroxide (40 cm³), maintaining the temperature below 30° C. The reaction mixture was stirred for 17 hours, filtered through celite, washing with the minimum of water, and the filtrate acidifed with 6N hydrochloric acid under ice-bath cooling. A solution of sodium nitrite (1.26 g) in water (10 cm³) was added dropwise to the stirred, cooled solution. The reaction mixture was allowed to warm to room temperature and after 1 hour extracted with ethyl acetate (3×50 ml). The combined extracts were washed with water and dried (MgSO₄). The solvent was removed under reduced pressure leaving a reddish-brown solid (2.3 g).

The solid was dissolved in dichloroethane (50 cm³), ethanol (2cm³) dimethylaminopyridine (0.8 g) and dicyclohexylcarbodiimide (1.35 g 6.6 mmol) were added and the mixture refluxed for 8 hours. After cooling to room temperature the dicyclohexylurea formed was removed by filtration and the filtrate diluted with chloroform (50 cm³), washed with water and dried (MgSO₄). The solvent was removed under reduced pressure leaving a dark brown viscous residue which was purified by column chromatography on silica gel eluting with hexane/ethyl acetate (3:1) giving compound 24, ethyl DL 2-[6-(2-chloro-4-trifluoromethylphenoxy) -1,2,3-triazolo[4,5,b]-pyridinyl-1]-propionate as an off-white solid, m.p. 91–92° C.

EXAMPLE 11

This example illustrates the preparation of Compound No. 30.

Compound No. 22, DL 2-[6-(2-chloro-4-trifluoromethylphenoxy) -1,2,3-triazolo[4,5-b]pyridinyl-1]propionic acid (0.50 g, 1.3 mmol) was suspended in dichloromethane (1.5 ml) and oxalyl chloride (0.4 ml, 4.6 mmol) and N,N-dimethylformamide (1 drop) were added. The reaction mixture was stirred at room temperature for 17 hours, and then the solvent was evaporated under reduced pressure.

The residue was taken up in diethyl ether (5ml) and benzyl alcohol (0.13ml, 1.3mmol) and triethylamine (excess) were added. The mixture was stirred at room temperature for 24 hours. The reaction mixture was diluted with diethyl ether, washed with water, dried (MgSO₄) and the solvent removed under reduced pressure The residue was further purified by flash column chromatography on silica gel eluting with hexane/ethyl acetate (2:1) to give Compound No. 30, benzyl DL 2-[6-(2-chloro-4-trifluoromethylphenoxy)- 1,2,3triazolo[4,5-b]pyridinyl-1]propionate (0.28g) as a colourless solid m.p 117–118° C.

Compound No. 31 was prepared by an analogous process using appropriate reactants.

EXAMPLE 12

This Example illustrates the preparation of Compound No. 32.

Compound No. 22, DL 2-[6-(2-chloro-4-trifluoromethylphenoxy)-1,2,3-triazolo[4,5-b]pyridinyl-1]p ropionic acid (0.80g, 2.1mmol) was dissolved in tetrahydrofuran (20ml) and N,N'-carbonyldiimidazole (0.48g, 3.0mmol) was added. The reaction mixture was stirred at room temperature for 2 hours. Gaseous ammonia was passed through the solution and after the initial exotherms had subsided the reaction mixture was stirred for a further 1 hour.

The solvent was evaporated under reduced pressure, the residue taken up in ethyl acetate and washed successively with saturated aqueous sodium carbonate solution and water. The organic extract was dried (MgSO₄) and evaporated under reduced pressure and the residue further purified by flash column chromatography on silica gel, eluting with ethyl acetate to give Compound No. 32, DL 2-[6-(2-chloro-4-trifluoromethylphenoxy)- 1,2,3-triazolo[4,5-b]pyridinyl-1]propionamide (0.18g) as a beige solid m.p. 150-152° C.

EXAMPLE 13

This Example illustrates the preparation of Compound 35 and 36.

Step A

Compound No. 22 DL-2-[6-(2-chloro-4-trifluoromethylphenoxy)-1,2,3triazolo[4,5-b]pyridinyl-1]propionic acid (0.50g, 1.3mmol) was suspended in dichloromethane (10ml) and oxalyl chloride (0.4ml, 4.6mmol) and N,N-dimethylformamide (1 drop) were added. The reaction mixture was stirred at room temperature for 17 hours, and then the solvent removed.

The residue was taken up in dichloromethane (10ml). 1,1-Dimethyl hydrazine (0.12ml, 1.5mmol) and triethylamine (0.12ml, 1.5mmol) were added and the mixture stirred at room temperature for 4 hours. The mixture was diluted with dichloromethane, washed with water, dried (MgSO₄) and evaporated under reduced pressure The residue was further purified by flash column chromatography on silica gel, eluting with ethyl acetate to give Compound No. 35, DL-2-[6-(2-chloro-4-trifluoromethylphenoxy)-1,2,3triazolo[4,5-b]pyridinyl-1]propionyl dimethylhydrazide (0.42g) as a colourless solid m.p 171–173° C.

Compound Nos. 34, 46 and 47 were prepared by an analogous process using appropriate reactants.

Step B

Compound No. 35, DL 2-[6-(2-chloro-4-trifluoromethylphenoxy) -1,2,3-triazolo[4,5-b]pyridinyl1]propionyl dimethylhydrazide (0.30g, 0.7mmol) was dissolved in methanol (10ml) and methyl iodide (1ml) was added. The mixture was kept in the dark at room temperature for 3 days. The solvent was evaporated and the residue triturated sequentially with diethyl ether and chloroform, the solid collected and dried under reduced pressure to give Compound No. 36, DL 2-[6-(2-chloro-4-trimethylhydrazinium iodide (0.10g) as a colourless solid m.p 174–175° C.

EXAMPLE 14

This Example illustrates the preparation of Compound No. 33.

Compound No. 22, DL 2-[6-(2-chloro-4-trifluoromethylphenoxy) -1,2,3-triazolo[4,5-b]pyridinyl-1]propionic acid (0.55g, 1.42mmol) was heated in refluxing thionyl chloride (10ml) for 1 hour. The reaction mixture was cooled and the solvent removed under reduced pressure. The residue was stirred with aqueous methylamine (2ml) for 1 hour and then poured into water and extracted with chloroform. The organic extracts were dried (MgSO$_4$) and evaporated under reduced pressure and the residue further purified by preparative thin layer chromatography on silica gel eluting with ethyl acetate to give Compound No. 33, methyl DL 2-[6-(2-chloro-4-trifluoromethylphenoxy)-1,2,3-triazolo [4,5-b]pyridinyl-1]propionamide (0.07g) as a beige solid m.p 211-212° C. (dec).

EXAMPLE 15

This Example illustrates the preparation of Compound No. 55.

Compound No. 39 DL 2-[6-(2-chloro-6-fluoro-4-trifluoromethylphenoxy) -1,2,3-triazolo[4,5-b]pyridyl-1]propionic acid (1.0g, 2.5mmol) and potassium hydroxide (0.83g, 14.8mmol) were stirred together in refluxing methanol (25ml) for 7 hours. The solution was allowed to cool to room temperature and the solvent was removed under reduced pressure. The residue was taken up in water (30ml) and extracted with diethyl ether (2×30ml). The organic extracts were combined, dried (MgSO$_4$) and evaporated under reduced pressure.

The residue (1.03g) was dissolved in a mixture of 1,2-dichloroethane (15ml) and methanol (2ml) and the solution cooled in an ice-bath. 4-Dimethylaminopyridine (0.33g, 2.7mmol) and dicyclohexylcarbodiimide (0.54g, 2.6mmol) were added and the mixture stirred for 17 hours, gradually warming to room temperature.

The mixture was filtered through celite and the filtrate evaporated under reduced pressure. Diethyl ether was added and the mixture filtered through celite once more. The filtrate was evaporated and the orange-brown residue was further purified by flash column chromatography on silica gel, eluting with ethyl acetate/60-80 petroleum ether (1:2) to give Compound No. 55, methyl DL 2-[6-(2-chloro-6-methoxy-4-trifluoromethylphenoxy) -1,2,3-triazolo[4,5-b]-pyridinyl-1]propionate (0.41g) as a gum.

EXAMPLE 16

This Example illustrates the preparation of compound 56.

Potassium hydroxide (0.04g, 0.7mml) was added to a solution of compound 55, methyl DL 2-[6-(2-chloro-6-methoxy-4-trifluoromethylphenoxy)-1,2,3-triazolo[4,5-b]-pyridinyl-1]propionate (0.28g, 0.65mmol) in tetrahydrofuran (6ml) and water (3ml) and the mixture heated under reflux for 3 hours. The mixture was cooled to room temperature, diluted with water and partitioned with diethyl ether. The aqueous solution was acidified with dilute aqueous hydrochloric acid and extracted with diethyl ether. The ethereal extract was dried (MgSO$_4$) and evaporated under reduced pressure and the residue was further purified by flash column chromatography on silica gel eluting with chloroform/methanol (9:1) to give compound 56, DL 2-[6-(2-chloro-6-methoxy-4-trifluoromethylphenoxy) -1,2,3,-triazolo[4,5-b]pyridinyl-1]propionic acid (0.09g) as a colourless solid m.p. 184-185°.

Biological Data

The herbicidal activity of the compounds was tested as follows:

Each compound in the appropriate concentration was incorporated into a 4% emulsion of methylcyclohexanone and 0.4% blend of 3.6 parts Tween 20 and 1 part Span 80. Tween 20 is a Trade Mark for a surface active agent comprising a condensate of 20 molar proportions of ethylene oxide with sorbitan laurate. Span 80 is a Trade Mark for a surface-active agent comprising sorbitan monolaurate. Formulation was effected by dissolving the compound in the requisite amount of solvent/surfactant blend. If necessary, glass beads were added, the total liquid volume adjusted to 5ml with water, and the mixture shaken to effect complete dissolution of the compound. The formulation so prepared, after removal of beads where necessary, was then diluted to final spray volume (45 ml) with water.

The spray compositions so prepared were sprayed onto young pot plants (post-emergence test) at a rate equivalent to 1000 liters per hectare. Damage to plants was assessed 13 days after spraying by comparison with untreated plants, on a scale of 0 to 9 where 0 is 0% damage, 1 is 1-5% damage, 2 is 6-15% damage, 3 is 16-25% damage, 4 is 26-35% damage, 5 is 36-59% damage, 6 is 60-69% damage, 7 is 70-79% damage, 8 is 80-89% damage and 9 is 90-100% damage.

In a test carried out to detect pre-emergence herbicidal activity, crop seeds were sown at 2 cm depth (i.e. Sb, Ct, Rp, Ww, Mz, Rc, Sy) and weed seeds at 1 cm depth beneath compost, and sprayed with the compositions at the rate of 1000 liters per hectare. 20 days after spraying, the seedlings in the sprayed plastic trays were compared with the seedlings in unsprayed control trays, the damage being assessed on the same scale of 0 to 9.

The results of the tests are given in Table I below.

TABLE III

| COMPOUND NO. | RATE OF APPLICATION | PRE- OR POST-EMERGENCE APPLICATION | TEST PLANTS (see Table IV) | | | | | | | | | | | | |
|---|---|---|---|---|---|---|---|---|---|---|---|---|---|---|---|
| | | | Sb | Rp | Ct | Sy | Mz | Rc | Ww | Pi | Ca | Ga | Am | Bd | Eh |
| 1 | 0.25 | Pre | 0 | 0 | 0 | 0 | 0 | 0 | 4 | 0 | 0 | — | 0 | 0 | 0 |
| | | Post | 3 | 2 | 2 | 4 | 2 | 2 | 2 | 2 | 0 | — | 5 | 3 | 4 |
| 2 | 0.25 | Pre | 0 | 0 | 0 | 0 | 0 | 0 | 0 | 0 | 0 | — | 0 | 0 | 0 |
| | | Post | 3 | 0 | 4 | 3 | 2 | 0 | 5 | 3 | 6 | — | 6 | 0 | 4 |
| 3 | 0.25 | Pre | 0 | 0 | 2 | 0 | 0 | 0 | 0 | 0 | 0 | — | 0 | 0 | 0 |
| | | Post | 0 | 3 | 5 | 0 | 0 | 0 | 0 | 0 | 5 | 4 | 8 | 2 | 5 |
| 4 | 0.25 | Pre | 2 | 3 | 0 | 0 | 0 | 0 | 0 | — | 0 | — | 3 | 1 | 0 |
| | | Post | 4 | 0 | 2 | 2 | 2 | 0 | 0 | 2 | 4 | 0 | 3 | 2 | 3 |
| 5 | 1 | Pre | 0 | 0 | 0 | 0 | 2 | 5 | 0 | 0 | 0 | — | 3 | 5 | 0 |
| | | Post | 5 | 6 | 3 | 3 | 3 | 0 | 0 | 5 | 5 | 3 | 6 | 3 | 5 |
| 6 | 0.25 | Pre | 0 | 0 | 0 | 0 | 0 | 0 | 0 | 0 | 0 | 0 | 0 | 0 | 0 |
| | | Post | 0 | 4 | 0 | 5 | 0 | 0 | 0 | 0 | 4 | 0 | 2 | 2 | 2 |
| 7 | 1 | Pre | 0 | 0 | 0 | 0 | 0 | 0 | 0 | 0 | 0 | — | 2 | 2 | 0 |
| | 0.25 | Post | 2 | 3 | 2 | 1 | 0 | 0 | 1 | 3 | 2 | — | 4 | 0 | 0 |

TABLE III-continued

| | | | | | | | | | | | | | | | |
|---|---|---|---|---|---|---|---|---|---|---|---|---|---|---|---|
| 8 | 1 | Pre | 4 | 0 | 0 | 0 | 0 | 0 | 0 | 0 | 9 | — | 9 | 4 | 2 |
| | 0.25 | Post | 4 | 2 | 3 | 3 | 2 | 2 | 0 | — | 6 | 3 | 6 | 4 | 4 |
| 9 | 1 | Pre | 0 | 0 | 0 | 0 | 0 | 0 | 0 | 0 | — | — | 7 | 0 | 0 |
| | 0.25 | Post | 7 | — | 5 | 5 | 0 | 1 | 1 | — | 9 | — | 9 | 3 | 5 |
| 10 | 1 | Pre | 0 | 0 | 0 | 0 | 0 | 0 | 0 | 0 | — | — | 9 | 2 | 0 |
| | 0.25 | Post | 3 | — | 6 | 2 | 2 | 0 | 0 | — | 9 | — | 8 | 3 | 5 |
| 11 | 0.25 | Pre | 0 | 0 | 0 | 0 | 0 | 5 | 0 | — | — | — | 9 | 0 | 0 |
| | 0.25 | Post | 3 | — | 6 | 8 | 6 | 2 | 2 | — | 9 | — | 9 | 3 | 5 |
| 12 | 1 | Pre | 0 | 0 | 0 | 0 | 3 | 8 | 0 | 5 | 9 | — | 9 | 8 | 3 |
| | 0.25 | Post | 9 | 5 | 8 | 2 | 5 | 3 | 3 | 7 | 9 | 5 | 9 | 7 | 8 |
| 13 | 1 | Pre | 9 | 1 | 0 | 0 | 6 | 8 | 0 | 6 | 9 | — | 9 | 3 | 6 |
| | 0.25 | Post | 9 | 6 | 9 | 5 | 5 | 3 | 2 | 8 | 9 | 9 | 9 | 9 | 9 |
| 14 | 1 | Pre | 8 | 6 | 0 | 0 | 5 | 8 | 0 | 0 | 9 | 0 | 9 | 9 | 7 |
| | | Post | 9 | 9 | 9 | 9 | 9 | 9 | 9 | 9 | 9 | 9 | 9 | 9 | 9 |
| 15 | 1 | Pre | 9 | 0 | 0 | 0 | 0 | 7 | 0 | 6 | 9 | — | 9 | 9 | 7 |
| | 0.25 | Post | 9 | 6 | 9 | 5 | 6 | 4 | 4 | 9 | 8 | 8 | 9 | 6 | 8 |
| 16 | 1 | Pre | 9 | 0 | 5 | 7 | 5 | 5 | 3 | — | 9 | — | 9 | 9 | 9 |
| | | Post | 9 | 5 | 9 | 9 | 8 | 4 | 8 | 9 | 9 | — | 9 | 9 | 9 |
| 17 | 1 | Pre | 9 | 0 | 0 | — | 0 | — | 0 | 9 | 9 | — | — | 8 | 9 |
| | | Post | 9 | 7 | 9 | 9 | 8 | 4 | 4 | — | 9 | — | 9 | 9 | 9 |
| 18 | 1 | Pre | 5 | 5 | 0 | 0 | 5 | 7 | 2 | — | — | — | 8 | 0 | 9 |
| | 0.25 | Post | 5 | 9 | 5 | 7 | 8 | 0 | 4 | — | 9 | — | 6 | 7 | 7 |
| 19 | 0.25 | Pre | 0 | 0 | 1 | 0 | 0 | 0 | 0 | — | — | — | 0 | 0 | 5 |
| | 0.625 | Post | 7 | 8 | 9 | 5 | 7 | 0 | 3 | — | 9 | 0 | 9 | 7 | 9 |
| 20 | 0.25 | Pre | 0 | 0 | 0 | 0 | 0 | 0 | 0 | — | — | — | 0 | 0 | 0 |
| | 0.625 | Post | 7 | 7 | 9 | 8 | 9 | 0 | 6 | — | 9 | — | 9 | 4 | 9 |
| 21 | 1 | Pre | 8 | 3 | 2 | 3 | 4 | 2 | 2 | — | 9 | — | 9 | 0 | 8 |
| | | Post | 8 | 4 | 8 | 9 | 5 | 3 | 3 | 9 | 9 | — | 9 | 3 | 8 |
| 21 | 1 | Pre | 8 | 3 | 2 | 3 | 4 | 2 | 2 | — | 9 | — | 9 | 0 | 8 |
| | | Post | 8 | 4 | 8 | 9 | 5 | 3 | 3 | 9 | 9 | — | 9 | 3 | 8 |
| 22 | 0.25 | Pre | 5 | 6 | 5 | 4 | 3 | 2 | 3 | 3 | 6 | — | 7 | 8 | 9 |
| | | Post | 9 | 9 | 9 | 9 | 9 | 7 | 9 | 9 | 9 | 8 | 9 | 9 | 9 |
| 23 | 0.25 | Pre | 0 | 0 | 0 | 0 | 0 | 3 | 0 | 7 | 9 | — | 9 | 3 | 9 |
| | 0.0625 | Post | 9 | 9 | 9 | 9 | 9 | 5 | 6 | 9 | 9 | — | 9 | 9 | 9 |
| 24 | 1 | Pre | 8 | 4 | 0 | 0 | 4 | 5 | 0 | 8 | 9 | 9 | 9 | 4 | 9 |
| | | Post | 9 | 9 | 9 | 9 | 9 | 8 | 9 | 9 | 9 | 9 | 9 | 9 | 9 |
| 25 | 1 | Pre | 8 | 8 | 6 | 0 | 3 | 7 | 0 | — | 9 | 0 | 9 | 9 | 9 |
| | 0.25 | Post | 9 | 9 | 9 | 9 | 9 | 5 | 8 | — | 9 | 8 | 9 | 9 | 9 |
| 26 | 1 | Pre | 9 | 7 | 5 | 2 | 5 | 3 | 1 | 9 | 9 | — | 9 | 9 | 9 |
| | 0.25 | Post | 9 | 9 | 9 | 9 | 9 | 6 | 7 | 9 | 9 | 9 | 9 | 6 | 9 |
| 27 | 0.25 | Pre | 0 | 0 | 4 | 2 | 2 | 0 | 0 | 6 | 3 | — | 9 | 9 | 9 |
| | | Post | 9 | 9 | 9 | 9 | 9 | 7 | 8 | 9 | 9 | 9 | 9 | 9 | 9 |
| 28 | 0.25 | Pre | 0 | 0 | 0 | 0 | 0 | 3 | 0 | — | 9 | 0 | 9 | 5 | 8 |
| | 0.0625 | Post | 9 | 9 | 9 | 9 | 9 | — | 9 | 9 | 9 | 9 | 9 | 9 | 9 |
| 29 | 1 | Pre | 6 | 5 | 0 | 0 | 3 | 8 | 0 | 9 | 9 | 0 | 9 | 9 | 9 |
| | 0.0625 | Post | 8 | 9 | 9 | 7 | 8 | 4 | 5 | — | 9 | 9 | 9 | 9 | 9 |
| 30 | 0.25 | Pre | 0 | 0 | 5 | 0 | 0 | 4 | 0 | — | 9 | 0 | 9 | 4 | 5 |
| | 0.0625 | Post | 9 | 5 | 9 | 8 | 8 | 5 | 6 | 9 | 8 | 8 | 9 | 9 | 9 |
| 31 | | | | | | | | | | | | | | | |
| 32 | 0.25 | Pre | 4 | 5 | 3 | 2 | 1 | 0 | 5 | 9 | 9 | — | 9 | 9 | 2 |
| | | Post | 9 | 7 | 9 | 9 | 9 | 4 | 8 | 9 | 9 | 9 | 9 | 9 | 9 |
| 33 | 1 | Pre | 6 | 6 | 2 | 1 | 5 | 5 | 4 | 9 | 9 | — | 9 | 8 | 9 |
| | 0.25 | Post | 9 | 7 | 5 | 6 | 5 | 3 | 3 | 8 | 9 | — | 9 | 6 | 9 |
| 34 | 1 | Pre | 5 | 5 | 0 | 0 | 0 | 2 | 4 | — | 9 | 5 | 9 | 5 | 6 |
| | 0.25 | Post | 8 | 7 | 9 | 7 | 6 | 3 | 4 | 9 | 9 | 9 | 9 | 9 | 9 |
| 35 | 1 | Pre | 7 | 5 | 5 | 0 | 4 | 5 | 0 | — | 9 | 0 | 9 | 8 | 9 |
| | 0.25 | Post | 7 | 9 | 9 | 8 | 9 | 3 | 4 | — | 9 | 6 | 9 | 9 | 9 |
| 36 | | | | | | | | | | | | | | | |
| 37 | 1 | Pre | 9 | 9 | 0 | 0 | 0 | 0 | 0 | 9 | 9 | — | 9 | 4 | 9 |
| | | Post | 9 | 9 | 9 | 6 | 9 | 3 | 8 | 9 | 9 | — | 9 | 7 | 9 |
| 38 | | | | | | | | | | | | | | | |
| 39 | 1 | Pre | 9 | 9 | 5 | 0 | 3 | 9 | 0 | 9 | 9 | 0 | 9 | 9 | 9 |
| | 0.25 | Post | 9 | 9 | 9 | 9 | 9 | 7 | 7 | — | 9 | 7 | 9 | 9 | 9 |
| 40 | | | | | | | | | | | | | | | |
| 41 | 1 | Pre | 8 | 9 | 3 | — | — | 9 | — | 9 | 9 | — | 9 | 9 | 9 |
| | 0.0625 | Post | 9 | 9 | 9 | 7 | 9 | 7 | 9 | — | 9 | 9 | 9 | 9 | 9 |

| COMPOUND NO. | RATE OF APPLICATION | PRE- OR POST-EMERGENCE APPLICATION | TEST PLANTS (see Table IV) | | | | | | | | | | | | |
|---|---|---|---|---|---|---|---|---|---|---|---|---|---|---|---|
| | | | Ip | Ab | Xa | Xs | Av | Al | Ag | Sh | St | Dg | Ec | Ce | |
| 1 | 0.25 | Pre | 0 | 0 | 0 | — | 0 | 0 | — | 0 | 0 | 0 | 0 | 0 | |
| | | Post | 3 | 5 | — | 0 | 0 | 0 | 0 | 2 | 0 | 0 | 3 | 0 | |
| 2 | 0.25 | Pre | 0 | 0 | 0 | — | 0 | 0 | — | 0 | 0 | 0 | 0 | 0 | |
| | | Post | 5 | 5 | — | 2 | 0 | 0 | 0 | 0 | 0 | 0 | 4 | 2 | |
| 3 | 0.25 | Pre | 0 | 0 | 0 | — | 0 | 0 | — | 0 | 0 | 0 | 0 | 0 | |
| | | Post | 5 | 5 | — | 5 | 0 | 0 | 0 | 0 | 0 | 0 | 0 | 0 | |
| 4 | 0.25 | Pre | 0 | 0 | 0 | — | 2 | 0 | — | 0 | 0 | 0 | 0 | 0 | |
| | | Post | 5 | 6 | — | 0 | 1 | 0 | 0 | 2 | 2 | 2 | 3 | 0 | |
| 5 | 1 | Pre | 0 | 5 | 0 | — | 3 | 3 | — | 0 | 0 | 0 | 0 | 0 | |
| | | Post | 5 | 5 | — | 5 | 5 | 0 | 0 | 5 | 9 | 4 | 0 | 0 | |
| 6 | 0.25 | Pre | 0 | 0 | 5 | — | 0 | 0 | — | 0 | 0 | 0 | 0 | 0 | |
| | | Post | 2 | 0 | — | 3 | 3 | 2 | 0 | 2 | 0 | 0 | 3 | 0 | |

TABLE III-continued

| # | Rate | Time | | | | | | | | | | | | |
|---|---|---|---|---|---|---|---|---|---|---|---|---|---|---|
| 7 | 1 | Pre | 0 | 0 | 0 | — | 0 | 0 | — | 0 | 0 | 7 | 0 | 0 |
|  | 0.25 | Post | 0 | 2 | — | 0 | 0 | 0 | — | 0 | 0 | 0 | 0 | 0 |
| 8 | 1 | Pre | 3 | 0 | 2 | — | 3 | 0 | — | 3 | 1 | 0 | 2 | 0 |
|  | 0.25 | Post | 8 | 4 | — | 5 | 0 | 0 | 0 | 4 | 2 | 2 | 3 | 0 |
| 9 | 1 | Pre | 0 | 0 | 0 | — | 0 | 0 | — | 0 | 0 | — | 0 | 0 |
|  | 0.25 | Post | 9 | 6 | — | 5 | 1 | 0 | 0 | 0 | 2 | 0 | 0 | 0 |
| 10 | 1 | Pre | 0 | 0 | 0 | — | 7 | 0 | — | 0 | 0 | 0 | 0 | 0 |
|  | 0.25 | Post | 9 | 7 | — | 6 | 0 | 0 | 0 | 2 | 4 | 0 | 0 | 0 |
| 11 | 0.25 | Pre | 0 | 0 | 0 | — | 0 | 0 | — | 3 | 5 | — | 5 | 0 |
|  | 0.25 | Post | 9 | 7 | — | 4 | 1 | 1 | 1 | 5 | 7 | 7 | 0 | 1 |
| 12 | 1 | Pre | 5 | 3 | 2 | — | 0 | 0 | — | 0 | 0 | 0 | 5 | 4 |
|  | 0.25 | Post | 9 | 6 | — | 6 | 4 | 3 | 4 | 0 | 3 | 3 | 7 | 2 |
| 13 | 1 | Pre | 6 | 4 | 0 | — | 0 | 0 | — | 2 | 0 | — | 8 | 6 |
|  | 0.25 | Post | 9 | 9 | — | 9 | 3 | 2 | 4 | 2 | 5 | 2 | 6 | 3 |
| 14 | 1 | Pre | 9 | 7 | 4 | — | 0 | 0 | — | 4 | 0 | 0 | 6 | — |
|  |  | Post | 9 | 9 | — | 9 | 6 | 5 | 6 | 9 | 9 | 9 | 9 | 9 |
| 15 | 1 | Pre | 4 | 2 | 2 | — | 0 | 0 | — | 2 | 0 | 0 | 5 | 4 |
|  | 0.25 | Post | 9 | 9 | — | 9 | 4 | 3 | 4 | 2 | 5 | 2 | 4 | 4 |
| 16 | 1 | Pre | 5 | 9 | 4 | — | 6 | 3 | — | 3 | 9 | — | 7 | 5 |
|  |  | Post | 9 | 9 | — | 9 | 6 | 2 | 7 | 6 | 9 | 7 | 8 | 5 |
| 17 | 1 | Pre | 0 | 9 | 0 | — | 3 | 3 | — | 2 | 9 | — | 9 | 0 |
|  |  | Post | 9 | 9 | — | 9 | 9 | 4 | 6 | 7 | 9 | 9 | 9 | 8 |
| 18 | 1 | Pre | 0 | 0 | 0 | — | 0 | 0 | — | 5 | 3 | 6 | 2 | 0 |
|  | 0.25 | Post | 9 | 3 | — | 9 | 5 | 1 | 0 | 9 | 9 | 9 | 7 | 0 |
| 19 | 0.25 | Pre | 0 | 0 | 0 | — | 0 | 0 | — | 3 | 0 | 0 | 0 | 0 |
|  | 0.625 | Post | 9 | 7 | — | 8 | 6 | 2 | 2 | 8 | 9 | 8 | 7 | 0 |
| 20 | 0.25 | Pre | 0 | 0 | 0 | — | 0 | 0 | — | 3 | 0 | 0 | 0 | 0 |
|  | 0.625 | Post | 9 | 9 | — | 5 | 5 | 2 | 2 | 6 | 9 | 8 | 6 | 0 |
| 21 | 1 | Pre | 4 | 7 | 0 | — | 4 | 1 | — | 3 | 4 | — | 7 | 2 |
|  |  | Post | 9 | 9 | — | 7 | 3 | 2 | 2 | 8 | 4 | 5 | 3 | 3 |
| 21 | 1 | Pre | 4 | 7 | 0 | — | 4 | 1 | — | 3 | 4 | — | 7 | 2 |
|  |  | Post | 9 | 9 | — | 7 | 3 | 2 | 2 | 8 | 4 | 5 | 3 | 3 |
| 22 | 0.25 | Pre | 2 | 6 | 2 | — | 6 | 5 | — | 5 | 5 | 0 | 4 | 2 |
|  |  | Post | 9 | 9 | — | 9 | 9 | 9 | 8 | 9 | 9 | 9 | 9 | 3 |
| 23 | 0.25 | Pre | 3 | 0 | 5 | — | 0 | 0 | — | 0 | 5 | 0 | 4 | 0 |
|  | 0.0625 | Post | 9 | 9 | — | 9 | 9 | 5 | 7 | 9 | 9 | 9 | 9 | 5 |
| 24 | 1 | Pre | 0 | 5 | 0 | — | 0 | 0 | — | 8 | 9 | 9 | 8 | — |
|  |  | Post | — | 9 | — | 9 | 9 | 9 | 9 | 9 | 9 | 9 | 9 | 7 |
| 25 | 1 | Pre | — | 9 | 2 | — | 2 | 6 | — | 9 | 9 | — | 6 | 2 |
|  | 0.25 | Post | 9 | 9 | — | 9 | 9 | 7 | 6 | 9 | 9 | 9 | 9 | 6 |
| 26 | 1 | Pre | 4 | 9 | 6 | — | 0 | 4 | — | 6 | 9 | — | 9 | 3 |
|  | 0.25 | Post | 9 | 9 | — | 9 | 8 | 5 | 3 | 9 | 9 | 7 | 9 | 3 |
| 27 | 0.25 | Pre | 0 | 8 | 0 | — | 5 | 4 | — | 4 | 7 | — | 0 | 0 |
|  |  | Post | 9 | 9 | — | 9 | 9 | 5 | 9 | 9 | 9 | 9 | 9 | 2 |
| 28 | 0.25 | Pre | 0 | 6 | 0 | — | 0 | 0 | — | 6 | 3 | — | 0 | 0 |
|  | 0.0625 | Post | 9 | 9 | — | 9 | 5 | 5 | 3 | 9 | 9 | 9 | 9 | 3 |
| 29 | 1 | Pre | 2 | 8 | — | 6 | 0 | 2 | — | 8 | 7 | — | 8 | 0 |
|  | 0.0625 | Post | 9 | 9 | — | 9 | 5 | 5 | 2 | 9 | 9 | 9 | 9 | 0 |
| 30 | 0.25 | Pre | 0 | 6 | 0 | — | 3 | 2 | — | 3 | 8 | — | 0 | 0 |
|  | 0.0625 | Post | 8 | 9 | — | 9 | 4 | 3 | 2 | 9 | 9 | 9 | 9 | 4 |
| 31 |  |  |  |  |  |  |  |  |  |  |  |  |  |  |
| 32 | 0.25 | Pre | 2 | 7 | 3 | — | 5 | 4 | — | 4 | 6 | — | 5 | 3 |
|  |  | Post | 9 | 9 | — | 9 | 5 | 2 | 4 | 8 | 8 | 4 | 4 | 3 |
| 33 | 1 | Pre | 2 | 9 | 2 | — | 3 | 4 | — | 5 | 5 | 6 | 7 | 3 |
|  | 0.25 | Post | 9 | 8 | — | 5 | 3 | 3 | 3 | 3 | 7 | 5 | 4 | 1 |
| 34 | 1 | Pre | 0 | 8 | 0 | — | 2 | 4 | — | 5 | 9 | — | 6 | 0 |
|  | 0.25 | Post | 9 | 7 | — | 7 | 9 | 2 | 2 | 6 | 9 | 9 | 5 | 2 |
| 35 | 1 | Pre | 0 | 9 | 0 | — | 0 | 0 | — | 8 | 6 | — | 6 | 0 |
|  | 0.25 | Post | 9 | 7 | — | 9 | 3 | 2 | 3 | 8 | 9 | 9 | 8 | 2 |
| 36 |  |  |  |  |  |  |  |  |  |  |  |  |  |  |
| 37 | 1 | Pre | 0 | 9 | 0 | — | 5 | 5 | — | 7 | 9 | 9 | 9 | 0 |
|  |  | Post | 9 | 9 | — | 9 | 9 | 8 | 8 | 9 | 9 | 9 | 9 | 5 |
| 38 |  |  |  |  |  |  |  |  |  |  |  |  |  |  |
| 39 | 1 | Pre | 1 | 8 | — | 0 | 1 | 3 | — | 8 | 8 | — | 9 | 1 |
|  | 0.25 | Post | 9 | 9 | — | 9 | 9 | 7 | 9 | 8 | 9 | 9 | 9 | 2 |
| 40 |  |  |  |  |  |  |  |  |  |  |  |  |  |  |
| 41 | 1 | Pre | 1 | 9 | — | 1 | 3 | 7 | — | 7 | 9 | — | 9 | — |
|  | 0.0625 | Post | 9 | 9 | — | 9 | 9 | 9 | 5 | 9 | 5 | 8 | 9 | 1 |

TABLE IV

| | Test Plants |
|---|---|
| Sb | Sugar beet |
| Rp | Rape |
| Ct | Cotton |
| Sy | Soybean |
| Mz | Maize |
| Ww | Winter wheat |
| Rc | Rice |
| Bd | *Bidens pilosa* |
| Ip | *Ipomoea lacunosa* (pre-emergence) |

TABLE IV-continued

| | Test Plants |
|---|---|
| | *Ipomoea hederacea* (post-emergence) |
| Am | *Amaranthus retroflexus* |
| Pi | *Polygonum aviculare* |
| Ca | *Chenopodium album* |
| Ga | *Galium aparine* |
| Xa | *Xanthium spinosum* |
| Xs | *Xanthium strumarium* |
| Ab | *Abutilon theophrasti* |
| Eh | *Euphorbia heterophylla* |

TABLE IV-continued

Test Plants

| | |
|---|---|
| Av | *Avena fatua* |
| Dg | *Digitaria sanguinalis* |
| Al | *Alopecurus myosuroides* |
| St | *Setaria viridis* |
| Ec | *Echinochloa crus-galli* |
| Sh | *Sorghum halepense* |
| Ag | *Agropyron repens* |
| Ce | *Cyperus esculentes* |

We claim:

1. A compound of formula (I):

$$Ar-W \cdots N \cdots N$$
$$R^2-C-R^3$$
$$X-R^4$$

in which
the dotted lines indicate the presence of two double bonds arranged so as to form a fused heteroaromatic ring system;
Ar is an optionally substituted aryl or aromatic heterocyclic ring;
W is O or $NR^1$, where $R^1$ is hydrogen or lower alkyl;
X is $(CH_2)_n$, CH=CH, $CH(OR^5)CH_2$, $COCH_2$; where n is 0, 1 or 2;
$R^2$ and $R^3$ are independently selected from H, optionally substituted alkyl, alkenyl or alkynyl, halogen, $NR^6N^7$ or $R^2$ and $R^3$ together with the carbon to which they are attached form an optionally substituted cycloalkyl group;
$R^4$ is $CO_2R^8$, CN, $COR^8$, $CH_2OR^8$, $CH(OH)R^8$, $CH(OR^8)R^9$, $CSNH_2$, $COSR^8$, $CSOR^8$, $CONHSO_2R^8$, $CONR^{10}R^{11}$, $CONHNR^{10}R^{11}$, $CONHN^+R^{10}R^{11}R^{12}R^{13}\,^-$, $CO_2^-R^{14+}$ or $COON=CR^{10}R^{11}$;
$R^{14+}$ is an agriculturally acceptable cation; and
$R^{13-}$ is an agriculturally acceptable anion;
$R^5$, $R^8$ and $R^9$ are independently selected from H or an optionally substituted alkyl, aryl, alkenyl or alkynyl group; and
$R^6$, $R^7$, $R^{10}$, $R^{11}$, and $R^{12}$ are independently selected from H or an optionally substituted alkyl, alkenyl, aryl or alkynyl group or any two of $R^6$, $R^7$, $R^{10}$, $R^{11}$, and $R^{12}$ together with the atom to which they are attached form a heterocyclic ring; or $R^{10}$ and $R^{11}$ taken together with the carbon to which they are attached form a cycloalkyl ring.

2. A compound according to claim 1 wherein Ar is a group of sub formula (i):

$$\begin{array}{c} R^{16'} \\ | \\ CF_3 \end{array} \Biggm/ J \quad (i)$$

wherein $R^{16'}$ is hydrogen or halo, and J is N or a group $CR^{17'}$ where $R^{17'}$ is hydrogen or halo.

3. A compound according to claim 1 wherein Ar is an optionally substituted pyrazole group.

4. A compound according to any one of the preceding claims wherein $R^4$ is selected from a group $CO_2R^8$, CN, $CH_2OR^8$, $CONR^{10}R^{11}$, $COON=CR^{10}R^{11}$ or $CONHN^+R^{10}R^{11}R^{12}R^{13}-$, where $R^8$, $R^{10}$, $R^{11}$, $R^{12}$ and $R^{13-}$are defined in claim 1.

5. A compound according to claim 4 where $R^4$ is a group $CO_2R^8$ where is $C_{1-6}$ alkyl.

6. A compound according to claim 1 where X is $(CH_2)_n$ where n is 0 or 1.

7. A compound according to claim 6 where n is 0.

8. A compound according to claim 1 where W is oxygen.

9. A herbicidal composition comprising a compound of formula (I) as defined in claim 1 in combination with a carrier or diluent.

10. A composition according to claim 10 which further comprises an additional herbicidal agent not of formula (I).

11. A method of killing or controlling the growth of unwanted plants which method comprises applying to the plants or to a locus thereof an effective amount of a compound of formula (I) as defined in claim 1.

* * * * *